(12) United States Patent
Hu et al.

(10) Patent No.: US 10,952,904 B2
(45) Date of Patent: Mar. 23, 2021

(54) ANTIMICROBIAL BANDAGE WITH NANOSTRUCTURES

(71) Applicant: International Business Machines Corporation, Armonk, NY (US)

(72) Inventors: Huan Hu, Yorktown Heights, NY (US); Minhua Lu, Mohegan Lake, NY (US); Vince Siu, Ontario (CA); Gustavo Alejandro Stolovitzky, Riverdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 445 days.

(21) Appl. No.: 15/823,637

(22) Filed: Nov. 28, 2017

(65) Prior Publication Data
US 2019/0159937 A1    May 30, 2019

(51) Int. Cl.
*A61F 13/00* (2006.01)
*A61F 13/02* (2006.01)
(Continued)

(52) U.S. Cl.
CPC .. *A61F 13/00063* (2013.01); *A61F 13/00021* (2013.01); *A61F 13/0246* (2013.01);
(Continued)

(58) Field of Classification Search
CPC .......... A61F 13/00021; A61F 13/00063; A61F 13/0246; A61F 13/0289; A61F 2013/00327; A61F 13/00; A61F 13/00089; A61F 13/00085; A61F 13/023; A61F 13/0266; A61F 2013/00361; A61F 2013/00259;
(Continued)

(56) References Cited

U.S. PATENT DOCUMENTS 5,116,620 A    5/1992  Chvapil et al.
6,426,066 B1   7/2002  Najafi et al.
(Continued)

FOREIGN PATENT DOCUMENTS

WO    2013007354 A1    1/2013

OTHER PUBLICATIONS

Ivanova, et al., "Bactericidal activity of black silicon," Nature Communications | 4:2838 | DOI: 10.1038/ncomms3838, Received Jun. 7, 2013, 7 pages.
(Continued)

*Primary Examiner* — Rachael E Bredefeld
*Assistant Examiner* — Caitlin A Carreiro
(74) *Attorney, Agent, or Firm* — Amin, Turocy & Watson, LLP (57) ABSTRACT

Bandage apparatus, methods, and antimicrobial bandages for facilitating wound healing by providing an antimicrobial functionality. A bandage apparatus includes a substrate with a first surface and a second surface opposing the first surface. An attachment mechanism and a nanostructure film are provided on the first surface. The attachment mechanism facilitates removably attaching the substrate to a part of a body comprising a wound. The nanostructure film includes a plurality of nanostructures that contact the wound without puncturing the wound when the substrate is attached to the part of the body comprising the wound.

16 Claims, 10 Drawing Sheets

(51) Int. Cl.
  *B29C 65/48* (2006.01)
  *B29C 39/26* (2006.01)
  *B81C 99/00* (2010.01)
  *B29C 35/02* (2006.01)
  *B29L 31/00* (2006.01)
  *B29C 59/02* (2006.01)

(52) U.S. Cl.
  CPC .......... *A61F 13/0289* (2013.01); *B29C 35/02* (2013.01); *B29C 39/26* (2013.01); *B29C 65/48* (2013.01); *B81C 99/0085* (2013.01); *A61F 2013/00327* (2013.01); *B29C 2059/023* (2013.01); *B29L 2031/753* (2013.01); *B81C 2201/036* (2013.01)

(58) Field of Classification Search
  CPC . A61F 15/008; B29C 2059/023; B29C 35/02; B29C 39/26; B29C 65/48; B29L 2031/753; B81C 2201/036; B81C 99/0085
  USPC ................ 602/41–43, 52; 128/888; 604/304; 427/2.31
  See application file for complete search history.

(56) References Cited

U.S. PATENT DOCUMENTS

| | | | |
|---|---|---|---|
| 6,690,959 | B2* | 2/2004 | Thompson .......... A61B 5/0006 600/372 |
| 8,563,117 | B2 | 10/2013 | Messersmith et al. |
| 9,164,198 | B2 | 10/2015 | Lee et al. |
| 9,561,136 | B2 | 2/2017 | Williams |
| 2009/0068288 | A1 | 3/2009 | Kruger |
| 2010/0063434 | A1 | 3/2010 | Naik |
| 2012/0220975 | A1 | 8/2012 | Chan et al. |
| 2014/0364819 | A1 | 12/2014 | VanDelden |
| 2015/0266986 | A1 | 9/2015 | Wang et al. |
| 2016/0212989 | A1* | 7/2016 | Juodkazis .............. A01N 25/34 |

OTHER PUBLICATIONS

BOYLE, "Bandage Changes Color to Indicate State of Wound Underneath," Popular Science, Nov. 5, 2010, 2 pages.
Nt, et al., "Prototype Development of the Intelligent Hydrogel Wound Dressing and Its Efficacy in the Detection of Model Pathogenic Wound Biofilms," Jun. 22, 2016;8(24):12 pages.

\* cited by examiner

ANTIMICROBIAL BANDAGE WITH NANOSTRUCTURES

TECHNICAL FIELD

This application generally relates to antimicrobial bandages with nanostructures, formation thereof, and usage thereof to facilitate wound healing.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. The subject disclosure relates to antimicrobial bandages with nanostructures, formation thereof, and usage thereof to facilitate wound healing.

According to an embodiment, bandage apparatus is provided. The bandage apparatus can facilitate healing a wound. The bandage apparatus can comprise a substrate comprising an attachment mechanism that facilitates removably attaching the substrate to a part of a body comprising the wound. The bandage apparatus can further comprise a nanostructure film provided on a surface of the substrate and configured to contact the wound when the substrate is attached to the part of the body comprising the wound, wherein the nanostructure film comprises a plurality of nanostructures. In various implementations, respective nanostructures of the plurality nanostructures comprise a nanospike geometry.

The physical structure of the nanostructures can be specifically tailored to facilitate mechanically puncturing and killing bacterial cells that grow on and/or around the wound. In this regard, the respective nanostructures of the plurality of nanostructures can comprise a proximal end on the surface of the substrate and a distal end that extends away from the proximal end, and wherein the respective nano structures have a diameter that tapers from the proximal end to the distal end. In one or more implementations, the distal end can have a first diameter between about 1.0 nanometer (nm) and about 200 nm. The proximal can have a second diameter between about 1.0 nm to about 1.0 micrometer (μm). The respective nanostructures can also have a height between about 100 nm and about 10.0 μm. The spacing or pitch between the respective nanostructures can further be between about 100 nm and about 2.0 μm.

In various implementations, the substrate and the nanostructure film can comprise a flexible material. In this regard, the nanostructure film and the nanostructures can be formed with a material that is rigid enough to puncture bacterial cells but flexible enough to bend over and around a curved surface of the body to which it is attached without breaking. In one or more implementations, the nanostructure film and nanostructures can comprise a polymer material.

In another embodiment, a method is provided. The method can be a method that facilitates forming an antimicrobial bandage comprising a plurality of nanostructures. The method can comprise etching a silicon wafer to form a plurality of silicon nanostructures, and generating a nanostructure mold using the silicon nanostructures, the nanostructure mold comprising a plurality of nanostructure pores respectively corresponding to the silicon nanostructures. The method can further comprise employing the nanostructure mold to generate a nanostructure film comprising a plurality of nanostructures respectively corresponding to the nanostructure pores, and adhering the nanostructure film to a surface of a bandage substrate, thereby generating the antibacterial bandage. The bandage substrate can comprise a flexible material that can removably attach to a part of a body comprising a wound. The nanostructure film can comprise a flexible polymer material.

In one implementation, the etching of the silicon wafer can comprise employing metal-assisted chemical etching. In another implementation, the etching can comprise employing laser interference lithography. The silicon wafer can be etched to generate the silicon nanostructures with a pitch between about 100 nm and about 2.0 μm and a height between about 100 nm and about 10.0 μm. The nanostructure mold can be used to generate the nanostructure film by applying a polymer material onto the nanostructure mold and filling the nanostructure pores with the polymer material, curing the polymer material after the applying, thereby generating the nanostructure film, and removing the nanostructure film from the nanostructure mold.

In one or more additional embodiments, an antimicrobial bandage is provided. The antimicrobial bandage can comprise: a substrate comprising an attachment mechanism that facilitates removably attaching the substrate to a part of a body comprising a wound; and nanospikes provided on a surface of the substrate configured to contact the wound when the substrate is attached to the part of the body comprising the wound, wherein the nanospikes have a structure that facilitates reducing bacterial growth associated with the wound, thereby facilitating the healing of the wound.

BRIEF DESCRIPTION OF THE DRAWINGS

Numerous embodiments, objects and advantages of the present invention will be apparent upon consideration of the following detailed description, taken in conjunction with the accompanying drawings, in which like reference characters refer to like parts throughout, and in which.

DETAILED DESCRIPTION

The following detailed description is merely illustrative and is not intended to limit embodiments and/or application or uses of embodiments. Furthermore, there is no intention to be bound by any expressed or implied information presented in the preceding Summary section or in the Detailed Description section.

The subject disclosure relates to antimicrobial bandages with nanostructures, formation thereof, and usage thereof to facilitate wound healing by providing an antimicrobial functionality. Reducing bacterial infection on wounds is crucial for wound healing and patient health. The disclosed subject matter provides a new bio-inspired approach for reducing bacterial infection associated with wounds using a bandage that comprises a nanostructure layer provided on a surface of the bandage that contacts the wound. The nanostructure layer can comprise a plurality of nanostructures having a nanospike geometry that extend away from the bandage such that the peaks of the nanospikes contact the wound site. The nanostructures can provide a mechanical mechanism that facilitates reducing bacterial growth on or around the wound. In particular, bacteria growing on or near the surface of the wound have been found to bind to the nanospikes and continue to grow toward and around the nanospikes. Once the bacterial membrane has grown to a threshold point on and between the nanospikes, the nanospikes puncture the bacterial membrane, thereby killing the bacterial cells.

The geometric structure of the nanostructure layer can be specifically tailored to provide the aforementioned mechanical mechanism that facilitates killing bacteria. For example, if the spacing or pitch between the respective nanostructures is too wide or too narrow, the nanospikes will not puncture the bacterial membrane. Likewise, if the tip or point of the nanostructures is too dull, the nanostructures will not pierce the bacterial membrane. In this regard, the respective nanostructures can have a nanospike geometry that tapers from the proximal end (the base of the nanostructure) to the distal end (the peak or tip of the nanostructure). In one or more implementations, the distal end can have a first diameter between about 1.0 nm and about 200 nm. The proximal end can have a second diameter between about 1.0 nm to about 1.0 µm. The respective nanostructures can also have a height between about 100 nm and about 10.0 µm. The spacing or pitch between the respective nanostructures can further be between about 100 nm and about 2.0 µm. Further, the material employed for the nanostructure layer and nanostructures can include a material that is rigid enough to puncture bacterial cells but flexible enough to bend over and around a curved surface of the body to which the antimicrobial bandage is attached without breaking. In one or more implementations, the nanostructure layer and nanostructures can comprise a polymer material.

In one or more embodiments, semiconductor fabrication techniques can be employed to form the subject nanostructure layers having the geometric structure described above at low cost. In this regard, a silicon substrate or waver can be etched using metal-assisted chemical etching or laser interference lithography to generate silicon nanostructures having the desired geometric structure. The silicon nanostructures can further be employed to form a nanostructure mold comprising nanostructure pores corresponding to the silicon nanostructures. This nanostructure mold can further be employed to generate nanostructure layers comprising nanostructures that correspond to the silicon nanostructures yet formed out of a suitable material, such as a polymer, for their subject application in antimicrobial bandages. The resulting polymer nanostructure layer can further be attached to a bandage, thereby generating the disclosed antimicrobial bandage. The type of bandage to which the polymer nanostructure layer is applied can vary. For example, in some implementations, the bandage can comprise an adhesive bandage, a wrap, or the like. The size of the bandage can also vary.

As described infra, the subject nanospike surfaces have been experimentally found to best kill bacteria under static conditions, making them particularly suitable for the subject antimicrobial application in bandages. In addition, because the nanostructures are extremely small in size relative to epithelial layers of the body, the nanostructure layer does not puncture or irritate the wound and associated epithelial layers. One or more embodiments described herein can kill bacteria provided by the nanostructure bandage layer and remain effective for extensive periods of time without re-application and are not susceptible to bacteria developing antibiotic resistance. Accordingly, with the subject antimicrobial bandages, as the wound heals itself, the nanospike surface can constantly kill bacteria or limit bacterial growth, thereby providing constant protection from the wound developing infection.

One or more embodiments are now described with reference to the drawings, wherein like referenced numerals are used to refer to like elements throughout. It should be appreciated that the various structures depicted in the drawings (e.g., the antimicrobial bandage apparatus, the nanostructure layer, the silicon nanospikes, the mold, etc.) are merely exemplary and are not drawn to scale. In the following description, for purposes of explanation, numerous specific details are set forth in order to provide a more thorough understanding of the one or more embodiments. It is evident, however, in various cases, that the one or more embodiments can be practiced without these specific details.

Figure 1:
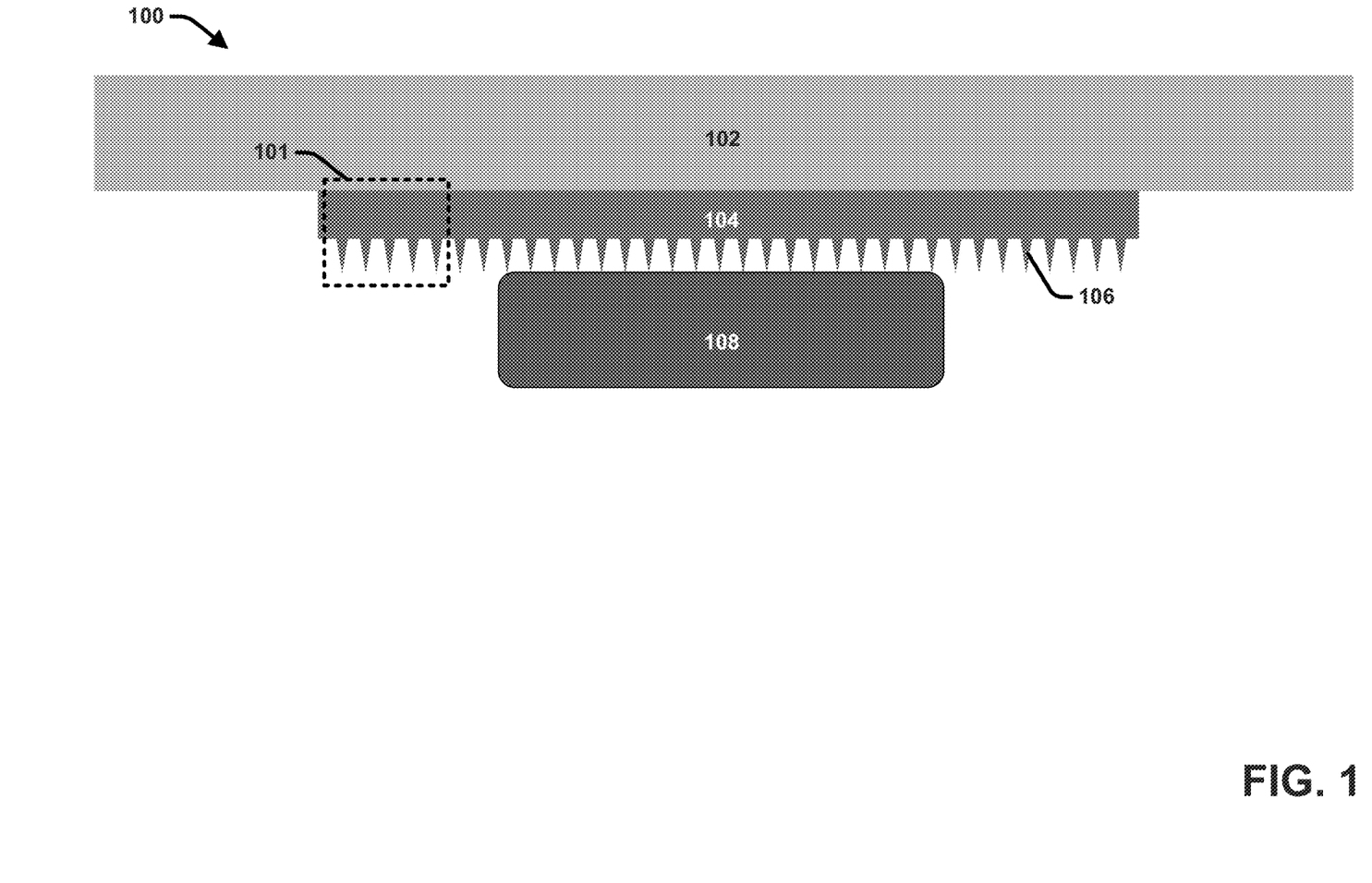
FIG. 1 presents an example antimicrobial bandage apparatus comprising a nanostructure layer in accordance with various embodiments described herein.

Turning now to the drawings, FIG. 1 presents an example antimicrobial bandage apparatus 100 comprising a nanostructure layer 104 in accordance with various embodiments described herein. In the embodiment shown, the antimicrobial bandage apparatus 100 comprises a bandage substrate 102 and a nanostructure layer 104 formed on a surface of the bandage substrate 102. The nanostructure layer 104 comprises a plurality of nanostructures 106 formed thereon that extend away from the surface of the bandage substrate 102.

In the embodiment shown, the antimicrobial bandage apparatus 100 is shown relative to a wound 108. The antimicrobial bandage apparatus 100 can facilitate wound healing by providing a mechanical mechanism that facilitates reducing bacterial growth on or around the wound 108 using the nanostructure layer 104. In this regard, the antimicrobial bandage apparatus 100 can be configured for application to a surface of a body comprising a wound (e.g., wound 108), such that the nanostructure layer 104 is positioned adjacent to the wound. In some embodiments, the tips (or distal ends) of nanostructures 106 can be configured to contact the wound in association with placement of the antimicrobial bandage apparatus 100 over the wound.

The nanostructures 106 of the nanostructure layer 104 can facilitate wound healing by mechanically killing bacteria cells that grow on or around the wound 108. In particular, bacteria that grows on or around the surface of the wound 108 have been found to latch onto the respective nanostructures 106 and continue to grow around and between the respective nanostructures 106. In this regard, the nanostructures effectively extract the bacteria membrane as it grows because the bacteria grab onto the tips of the nanostructures 106 and then continue to grow up the side surfaces of the nanostructures 106. At a certain point, a threshold is reached and the nanostructures 106 puncture the bacterial membrane, thereby killing the bacteria.

The aforementioned mechanical mechanism that facilitates killing bacterial provided by the nanostructure layer 104 is based in part on the geometric structure of the nanostructure layer 104. In this regard, the size, structure and spacing of the nanostructures 106 can be specifically selected to facilitate growth of bacterial on and around the nanostructures in a manner that results in puncturing of the bacterial membrane. For example, if the spacing or pitch between the respective nanostructures 106 is too wide or too narrow, the nanostructures will not puncture the bacterial membrane. Likewise, if the tips of the nanostructures are too dull, the nanostructures will not pierce the bacterial membrane.

Figure 2:
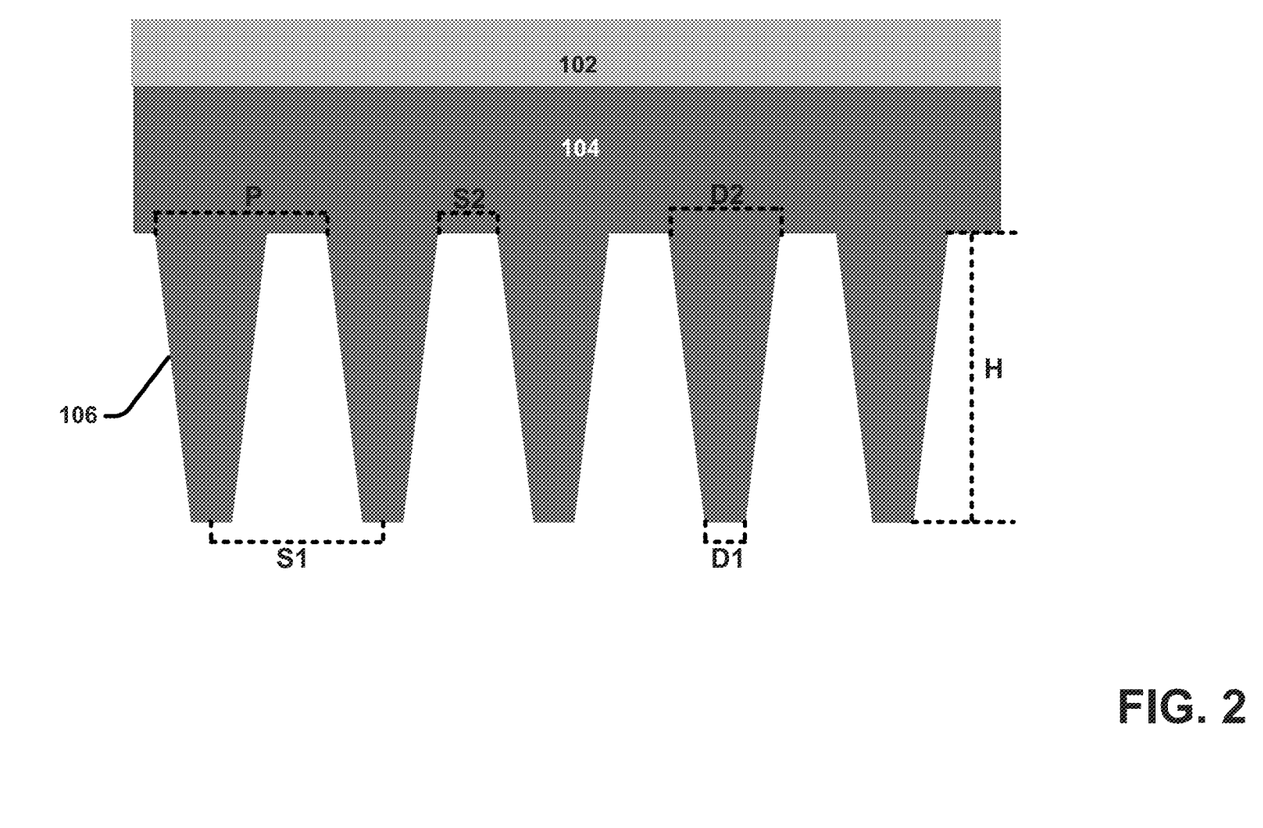
FIG. 2 presents an enlarged view of a portion of the nanostructure layer of an antimicrobial bandage apparatus in accordance with various embodiments described herein.

FIG. 2 presents an enlarged view of the portion of the nanostructure layer 104 shown in call out box 101 of FIG. 1. With reference to FIGS. 1 and 2, in one or more embodiments, the respective nanostructures 106 can have a nanospike geometry that tapers from the proximal end (the base of the nanostructure) to the distal end (the peak or tip of the nanostructure). In this regard, the diameter of the distal end can be smaller than the diameter of the proximal end. In one embodiment, the distal end can have a first diameter $D1$ between about 1.0 nm and about 200 nm. The proximal end can have a second diameter $D2$ between about 1.0 nm to about 1.0 µm. The respective nanostructures can also have a height $H$ between about 100 nm and about 10.0 µm. The pitch $P$ between the respective nanostructures can further be between about 100 nm and about 2.0 µm. In another embodiment, the distal end can have a first diameter $D1$ between about 1.0 nm and about 100 nm. The proximal end can have a second diameter $D2$ between about 1.0 nm to about 500 nm. The respective nano structures can also have a height $H$ between about 500 nm and about 5.0 µm. The pitch $P$ between the respective nanostructures can further be between about 100 nm and about 1.0 µm. Still in yet another embodiment, the distal end can have a first diameter $D1$ between about 10.0 nm and about 70 nm. The proximal end can have a second diameter $D2$ between about 100.0 nm to about 300 nm. The respective nanostructures can also have a height $H$ between about 800 nm and about 2.0 µm. The pitch $P$ between the respective nanostructures can further be between about 200 nm and about 800 nm.

In the embodiment shown, respective nanostructures can have a peak to peak distance of $S1$ and a spacing defined by $S2$. In some implementations, the peak to peak distance $S1$ can be the same or substantially the same distance as the pitch $P$. The spacing distance $S2$ between the bases of the respective nanostructures 106 can be between about between about 1.0 nm to about 1.0 µm in one embodiment. In another embodiment, $S2$ can be between about 50 nm to about 800 nm. In another embodiment, $S2$ can be between about 200 nm to about 500 nm. The various nanostructure dimensions (e.g., dimensions for $D1$, $D2$, $H$, $P$, $S1$ and $S2$) of the nanostructure layer 104 and associated nanostructures 106 described herein provide statistical means of suitable dimensions. However, it should be appreciated that in implementation with a bandage, these dimensions can be adapted as appropriate and the subject nanostructure layer 104 and associated nanostructures 106 are not limited to the dimensions described above. In some embodiments, the dimensions of the nanostructures 106 and nanostructure layer 104 can be tailored to kill different types of bacteria.

The material employed for the nanostructure layer 104 and nanostructures 106 can include a material that is rigid enough to puncture bacterial cells but flexible enough to bend over and around a curved surface of the body to which the antimicrobial bandage is attached without breaking. In one or more implementations, the nanostructure layer 104 and nanostructures can comprise a polymer material. Some suitable materials for the nanostructure layer 104 and the nanostructures 106 can include but are not limited to: maltose, carboxymethylcellulose, amylopectin, poly(methylvinylether/maleic anhydride), sodium hyaluronate, chondroitin sulphate/dextrin, sodium alginate, and hydroxypropyl cellulose, PET, polyimide, polydimethylsiloxane (PDMS), polystyrene (PS), polyethylene, polyurethane, polycarbonate, carbon nanotubes, nanowires, nanoparticles, acrylic, epoxy, and hydrogel.

The bandage substrate 102 and the mechanism for applying the antimicrobial bandage apparatus 100 to a surface of a body comprising a wound 108 can vary. For example, the antimicrobial bandage apparatus 100 can be adapted to facilitate healing of wounds of various shapes, sizes and bodily locations. The antimicrobial bandage apparatus 100 can further be adapted for application to wounds on humans as well as animals. In some implementations, the bandage substrate 102 can comprises a thin flexible layer of material configured to bend or wrap around parts of a body comprising a wound. For example, the bandage substrate 102 can comprise a polymer material, a rubber material, a fabric, a paper based material and the like. In one or more embodiments, the antimicrobial bandage apparatus 100 can be configured to removably attach to the surface of a body comprising a wound. In this regard, the antimicrobial bandage apparatus 100 can be configured for application to a wound for a period of time that facilitates healing the wound. The antimicrobial bandage apparatus 100 can also be removed and replaced with a new antimicrobial bandage apparatus every $N$ hours (e.g., 24 hours, 48 hours, etc.), which can vary depending on the type of wound and location of the wound.

Figure 3:
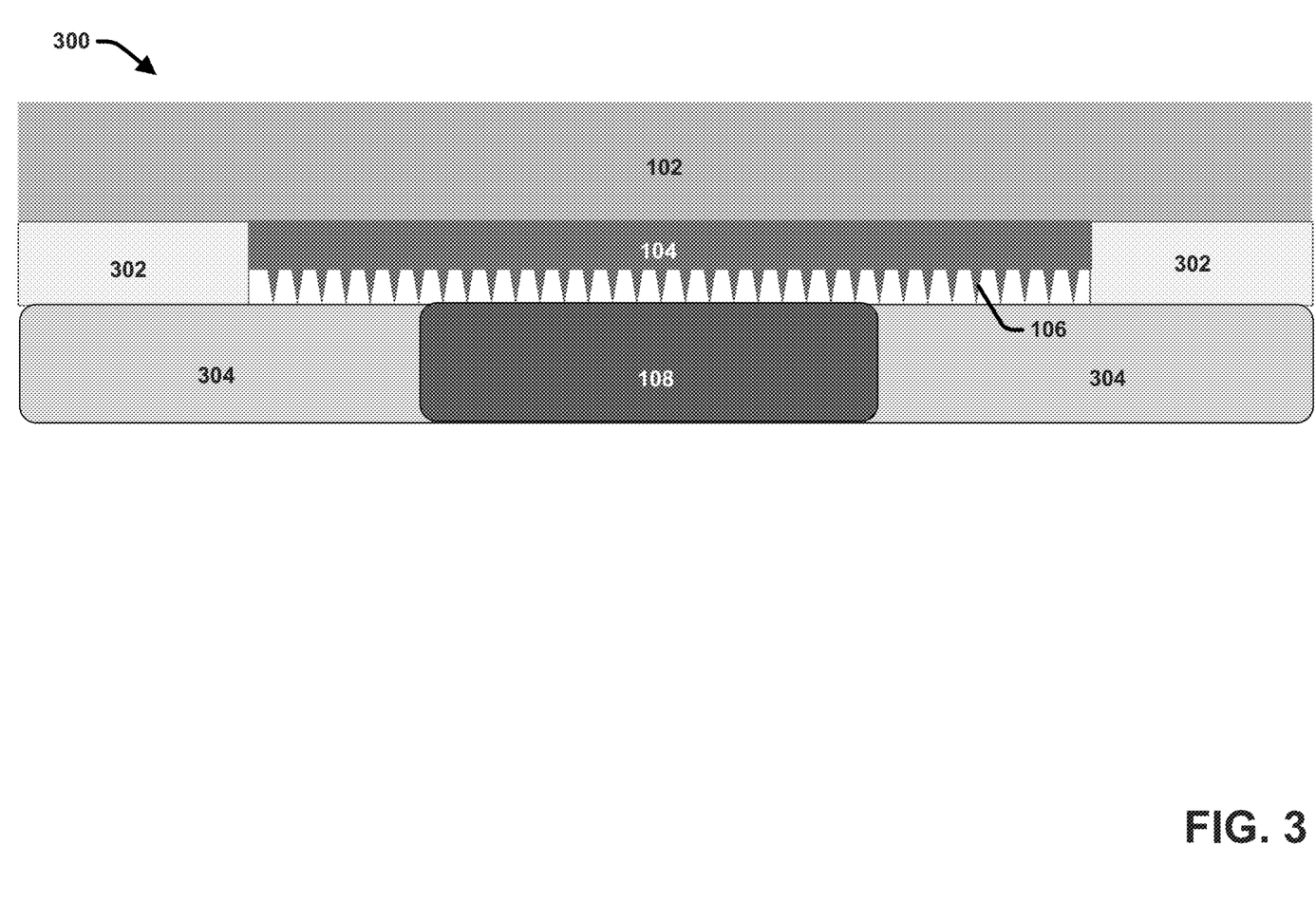
FIG. 3 presents another example antimicrobial bandage apparatus comprising a nanostructure layer in accordance with various embodiments described herein.

For example, FIG. 3 presents another example antimicrobial bandage apparatus 300 comprising a nanostructure layer in accordance with various embodiments described herein. The antimicrobial bandage apparatus 300 can comprise same or similar features and functionalities as antimicrobial bandage apparatus 100 with the addition of and adhesive layer 302. The adhesive layer 302 can be formed on the same surface of the bandage substrate comprising the nanostructure layer 104 and formed around the nanostructure layer 104. The adhesive layer 302 can comprise an adhesive material that facilitates removably attaching the antimicrobial bandage apparatus 300 to the surface of a body comprising a wound. For example, in the embodiment shown, the antimicrobial bandage apparatus 300 is attached to the upper epithelial layer 304 around the wound via the adhesive layer 302.

Figure 4:
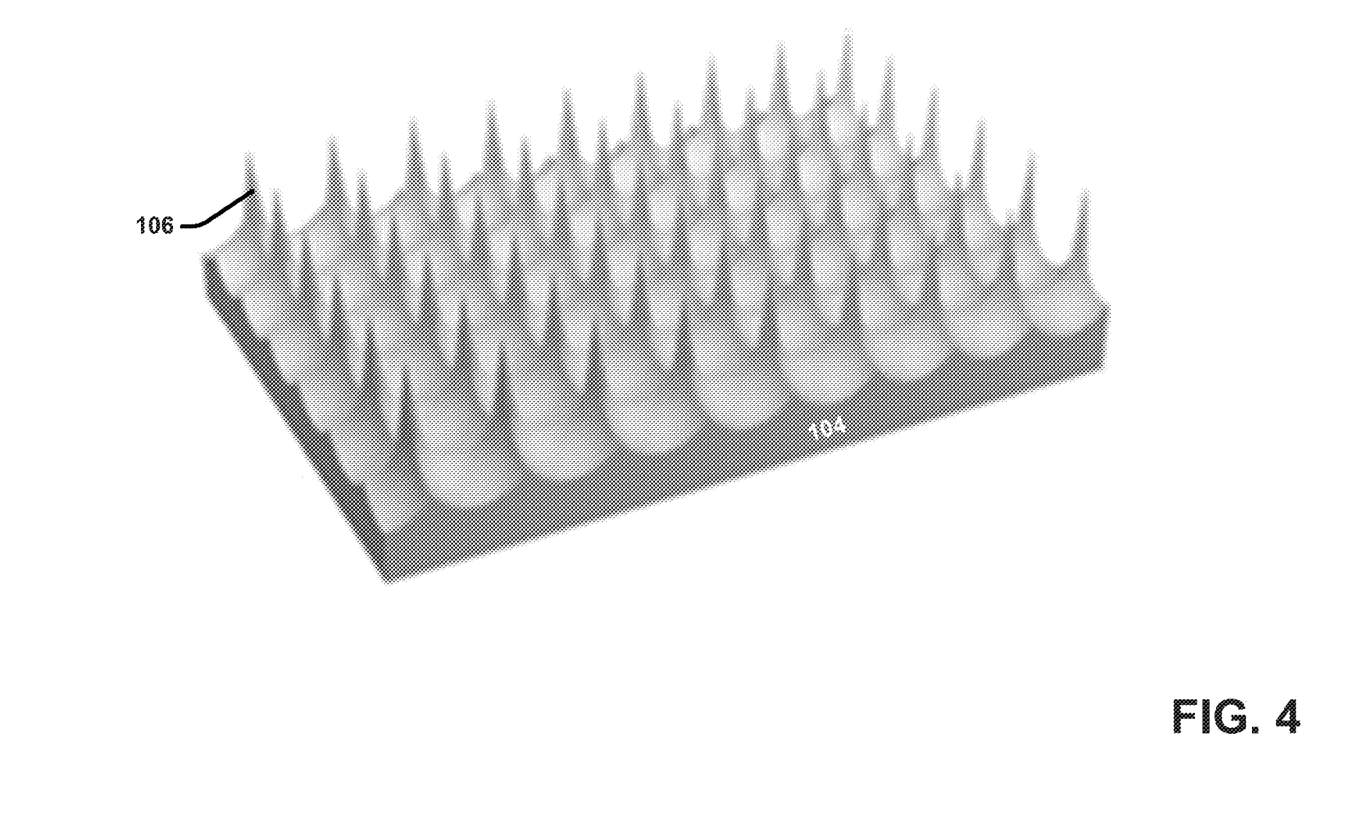
FIG. 4 presents a three-dimensional view of an example nanostructure layer of an antimicrobial bandage apparatus in accordance with various embodiments described herein.

FIG. 4 presents a three-dimensional view of an example nanostructure layer 104 of an antimicrobial bandage apparatus (e.g., antimicrobial bandage apparatus 100, 300 and the like) in accordance with various embodiments described herein. The nanostructure layer 104 comprises a plurality of nanostructures 106 that extend therefrom and respectively having a nanospike geometry. In the embodiment shown, the nanostructures 106 are arranged in organized and evenly spaced rows and columns. The dimensions and spacing of the respective nanostructures 106 can be commensurate with that described with reference to FIG. 2. In other embodiments, the arrangement of the nanostructures 106 can be non-uniform so long as the statistical means of the dimensions and spacing of the respective nanostructures are commensurate with that described with reference to FIG. 2. In other embodiments, the arrangement of the nanostructures 106 can vary at different locations of a bandage. In other embodiments, the arrangement of the nanostructures 106 can be non-square arrays.

Figure 5A:
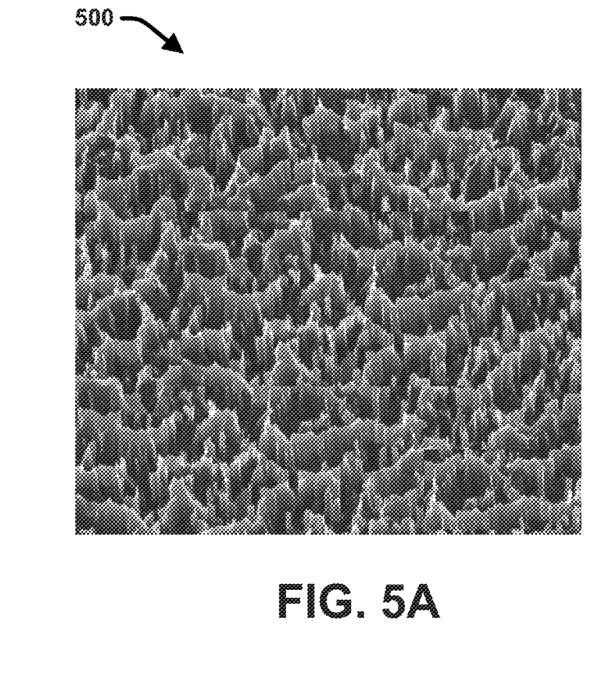
FIG. 5A presents a microscopic view of an example nanostructure layer in accordance with various embodiments described herein.
Figure 5B:
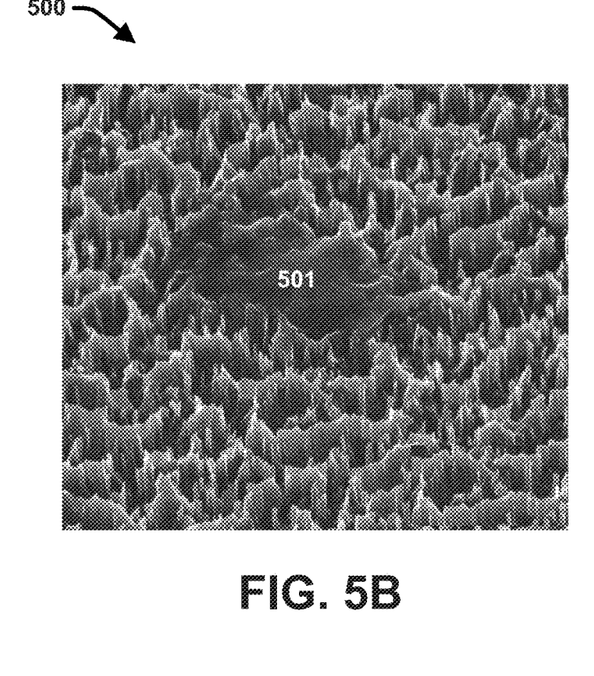
FIG. 5B presents another microscopic view of the example nanostructure layer yet having rupture bacterial membrane formed thereon in accordance with various embodiments described herein.

FIGS. 5A and 5B presents microscopic views of an example nanostructure layer 500 in accordance with various embodiments described herein. In one or more embodiments, nanostructure layer 500 can include same or similar features and functionalities as nanostructure layer 104. In the embodiment shown, the nanostructure layer 500 comprises a plurality of irregular or non-uniform nanostructures. The material, dimensions and spacing of the respective nanostructures can be commiserate with that described with reference to FIG. 2. The nanostructure layer 500 can thus be employed to facilitate reducing bacterial growth associated with wounds when used in antimicrobial bandages as described herein (e.g., antimicrobial bandage apparatus 100, 300 and the like).

For example, FIG. 5A presents a microscopic view of the example nanostructure layer 500 without exposure to bacteria. FIG. 5B presents another microscopic view of the example nanostructure layer 500 having been exposed to bacteria (e.g., in association with usage in an antimicrobial bandage apparatus 100 that was applied to a wound). In the embodiment shown in FIG. 5B, the nanostructure layer 500 has ruptured bacteria 501 formed thereon as a result of growth of the bacteria on and around the nanospikes of the nanostructure layer 500. For example, live bacterial cells have a uniform shape, such as a rod shape or the like. In the embodiment shown, the bacterial membrane has been ruptured by the nanospikes of the nanostructure layer 500, thereby causing the bacterial membrane to lose its uniform shape and kill the bacterial cells.

Figure 6A:
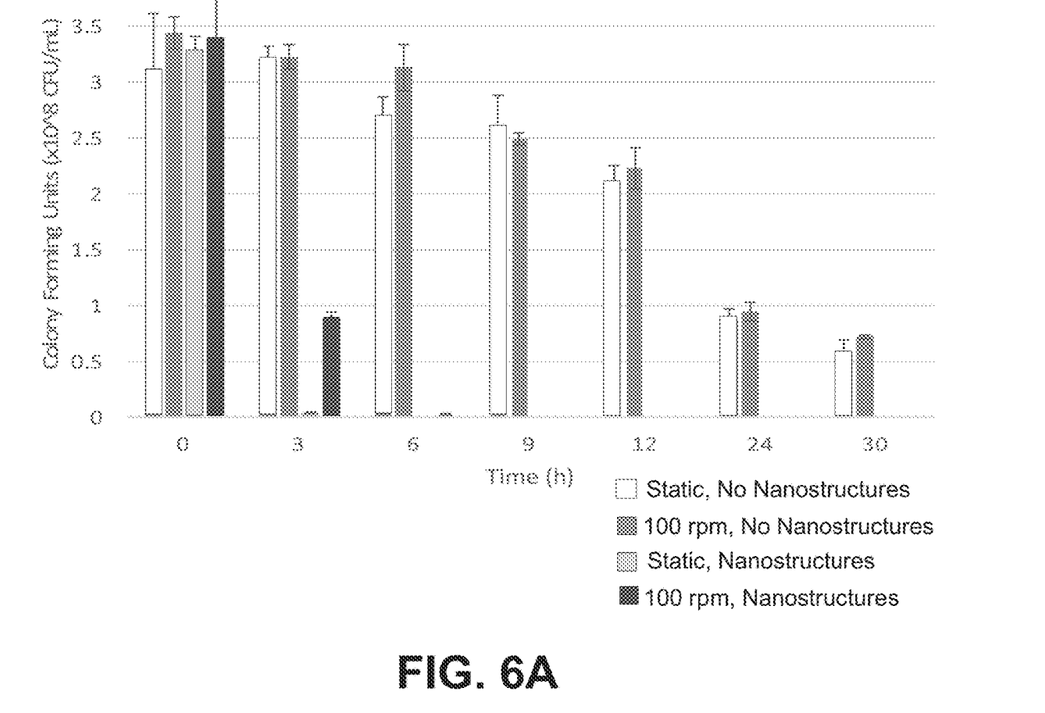
FIGS. 6A and 6B provide graphical illustrations demonstrating experimental performance of a nanostructure layer with respect to reducing bacterial growth under static and rotating conditions in accordance with various embodiments described herein.
Figure 6B:
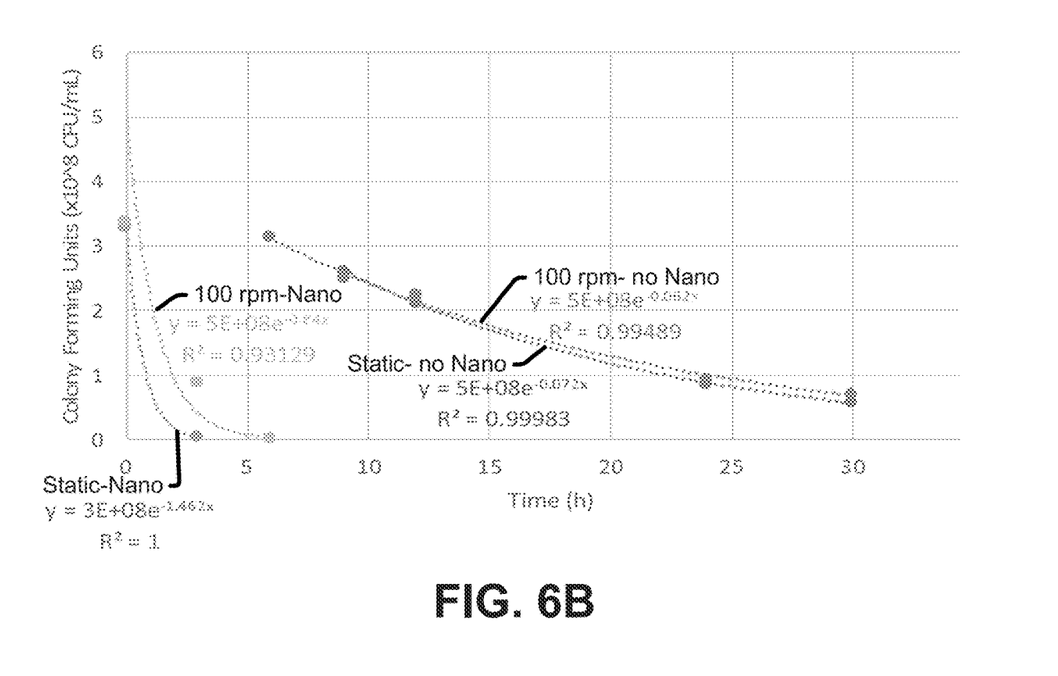

FIGS. 6A and 6B provide graphical illustrations demonstrating experimental performance of a nanostructure layer with respect to reducing bacterial growth under static and rotating conditions in accordance with various embodiments described herein. The experimental data reflected in the graphs of FIGS. 6A and 6B represents an amount of colony forming bacterial units present over time on different substrates with and without nanostructure layers (e.g., nanostructure layer 104 and the like) under static and rotating conditions. As shown in FIGS. 6A and 6B, initial findings suggest that the nanospikes are more effective at killing bacteria in static mode compared to a sample of nanospikes run at 100 revolutions per minute (rpm). This finding is novel and relevant for wound dressings, as dressings will often be used in static state.

Figure 7A:
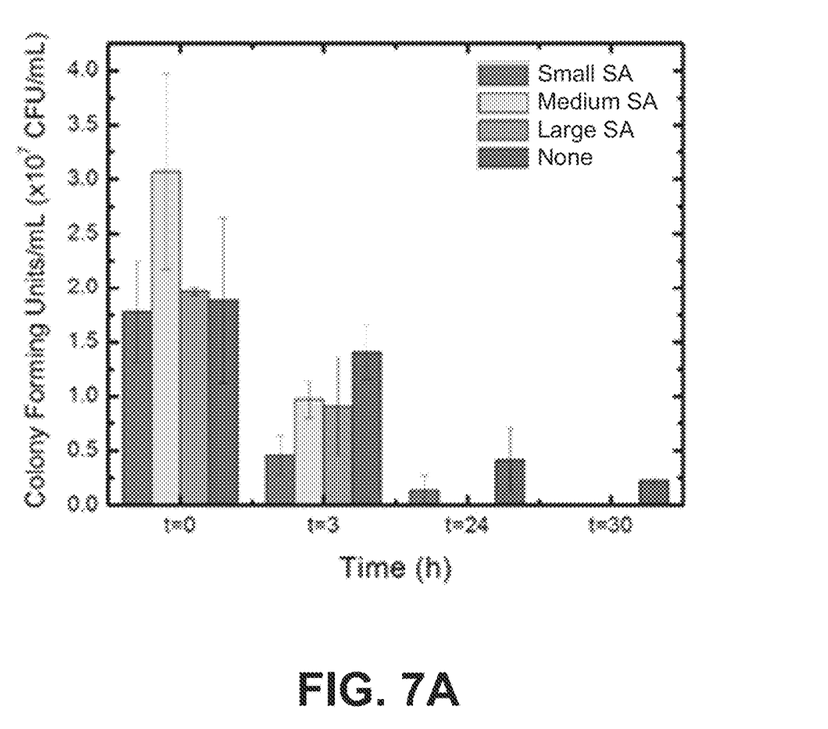
FIGS. 7A and 7B provide graphical illustrations demonstrating experimental performance nanostructures layer with different surface areas with respect to reducing bacterial growth in accordance with various embodiments described herein.
Figure 7B:
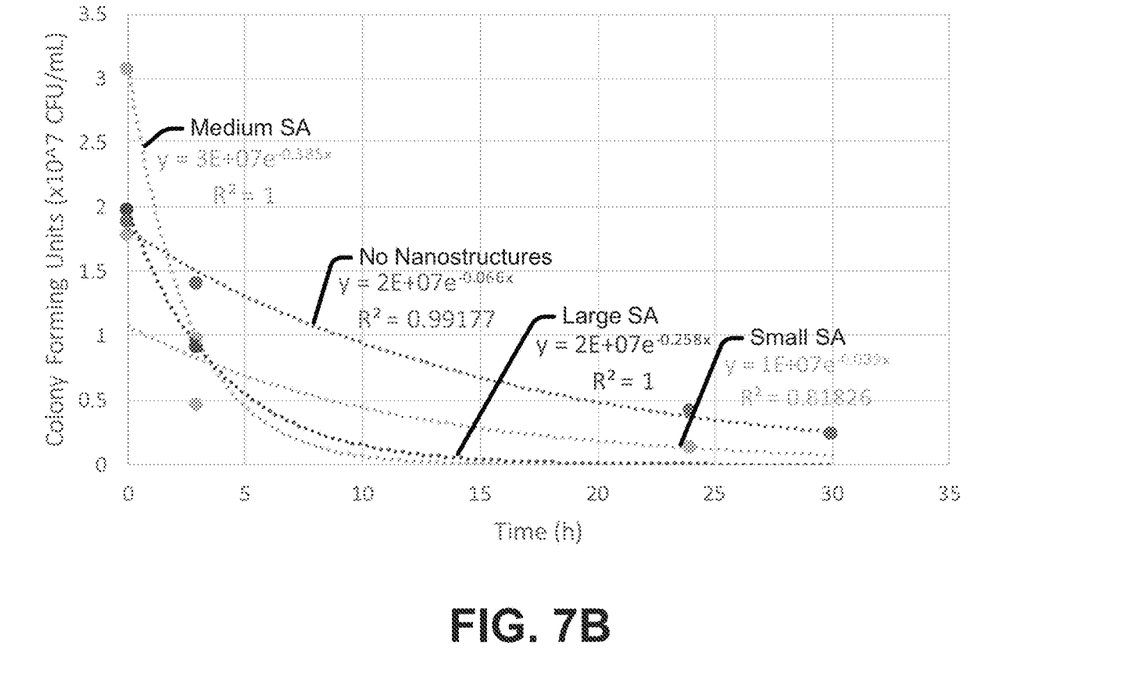

FIGS. 7A and 7B provide graphical illustrations demonstrating experimental performance nanostructures layer with different surface areas with respect to reducing bacterial growth in accordance with various embodiments described herein. The experimental data reflected in the graphs of FIGS. 7A and 7B represents an amount of colony forming bacterial units over time present on different substrates with different surface areas (SA) of nanostructures. As shown in FIGS. 7A and 7B, initial findings suggest that a larger surface area of nanospikes are more effective at killing bacteria than smaller surface areas. This finding is novel, and can be used to design wound dressings with optimal antimicrobial effectiveness.

Figure 8:
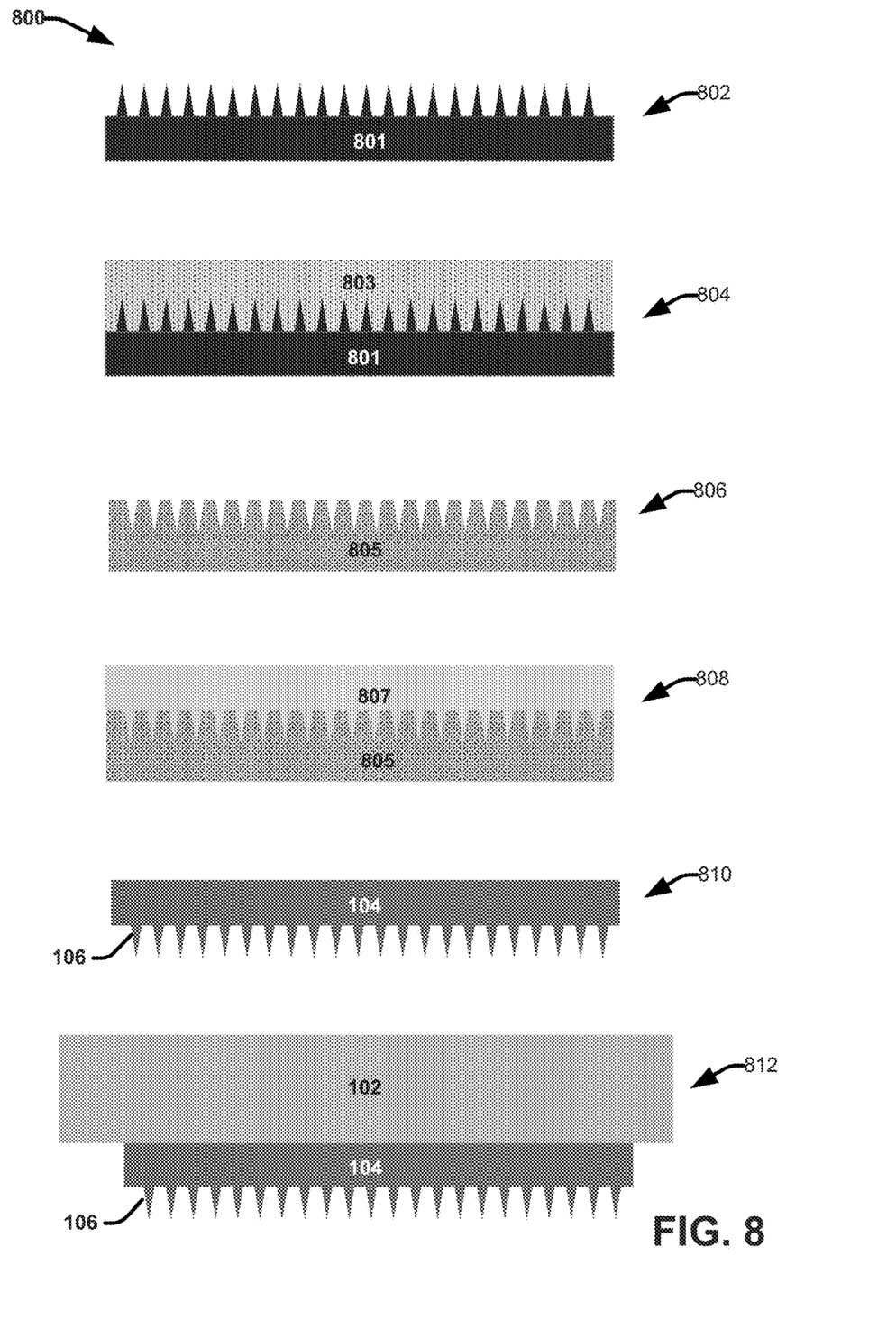
FIG. 8 provides a visual flow diagram of an example process that facilitates fabricating an antimicrobial bandage apparatus comprising a nanostructure layer in accordance with various embodiments described herein.

FIG. 8 provides a visual flow diagram of an example process 800 for fabricating an antimicrobial bandage apparatus comprising a nanostructure layer in accordance with various embodiments described herein. In one or more embodiments, semiconductor fabrication techniques can be employed to form the subject nanostructure layers having the geometric structure described herein at low cost. In this regard, as shown at 802, a silicon wafer can be initially patterned using one or more low cost semiconductor fabrication techniques to generate a silicon nanospike substrate 801. In one embodiment, the silicon wafer can be etched using metal-assisted chemical etching to generate the silicon nanospike substrate 801. In another embodiment, the silicon wafer can be patterned using laser interference lithography to generate the silicon nanospike substrate 801. The silicon nanospike substrate comprises a plurality of silicon nanospikes having the desired geometric properties of the nanostructures for the nanostructure layer 104. In this regard, the silicon nanospikes can have the same or substantially the same size, shape, pitch and spacing as the nanostructures 106 described with reference to FIG. 2.

The silicon nanospike substrate 801 can then be employed to generate a mold 805 having nanopores that correspond to the silicon nanospikes. Using a suitable molding material. For example, the mold material 803 can include an epoxy capable of being cured and hardened by ultraviolet (UV) light. Other suitable molding materials can include but are not limited to: PDMS, PS, polyethylene, polyurethane, polycarbonate, carbon nanotubes, nanowires, nanoparticles, acrylic, epoxy, and hydrogel. For example, at 804, the silicon nanospike substrate 801 can be covered with a mold material 803 in a malleable form (e.g., a liquid form, a semiliquid form, a gel form, and the like) such that the mold material 803 completely forms on and around the silicon nanospikes. The mold material 803 can further be cured (e.g., by UV light) or otherwise hardened to form a mold 805 which can subsequently be removed from the silicon nanospike substrate at 806. The resulting mold 805 can comprise nanostructure pores that correspond to the silicon nanospikes of the silicon nanospike substrate 801.

The mold 805 can further be employed to generate the nanostructure layer 104. For example, at 808, a nanostructure layer material 807 in a malleable form (e.g., as an epoxy) can be molded onto the mold 805 (or vice versa), such that the nanostructure layer material 807 fills the nanostructure pores of the mold 805. In one or more embodiments, the nanostructure layer material 807 can comprise an epoxy polymer capable of being cured by UV light. Once the nanostructure layer material 807 has filled the nanopores of the mold 805, the nanostructure layer material 807 can then be hardened (e.g., via curing with UV light) to generated the nanostructure layer 104. At 810, the nanostructure layer 104 can subsequently be removed from the mold 805. Then at 812, the bandage substrate 102 can be attached to the nanostructure layer 104 (or vice versa) on the side of the nanolayer that is opposite the nanostructures 106.

In other embodiments, various alternative techniques can be employed to generate a nanospike layer corresponding to the nanospike substrate 801. For example, other techniques for forming the nanostructures can include various forms of etching, laser machining, and self-assembly. Further the material employed for a nanostructure layer corresponding to the silicon nanospike substrate 801 can include but are not limited to: polycarbonate, polyimide, epoxy, metal, glass, cellulose, ceramic, and composites. In some embodiments, a nanospike substrate corresponding to the silicon nanospike substrate 801 can comprise a natural object or material found in nature with similar structure and dimensions as the silicon nanospike substrate (e.g., such as dimensions similar to those described with reference to FIG. 2).

Figure 9:
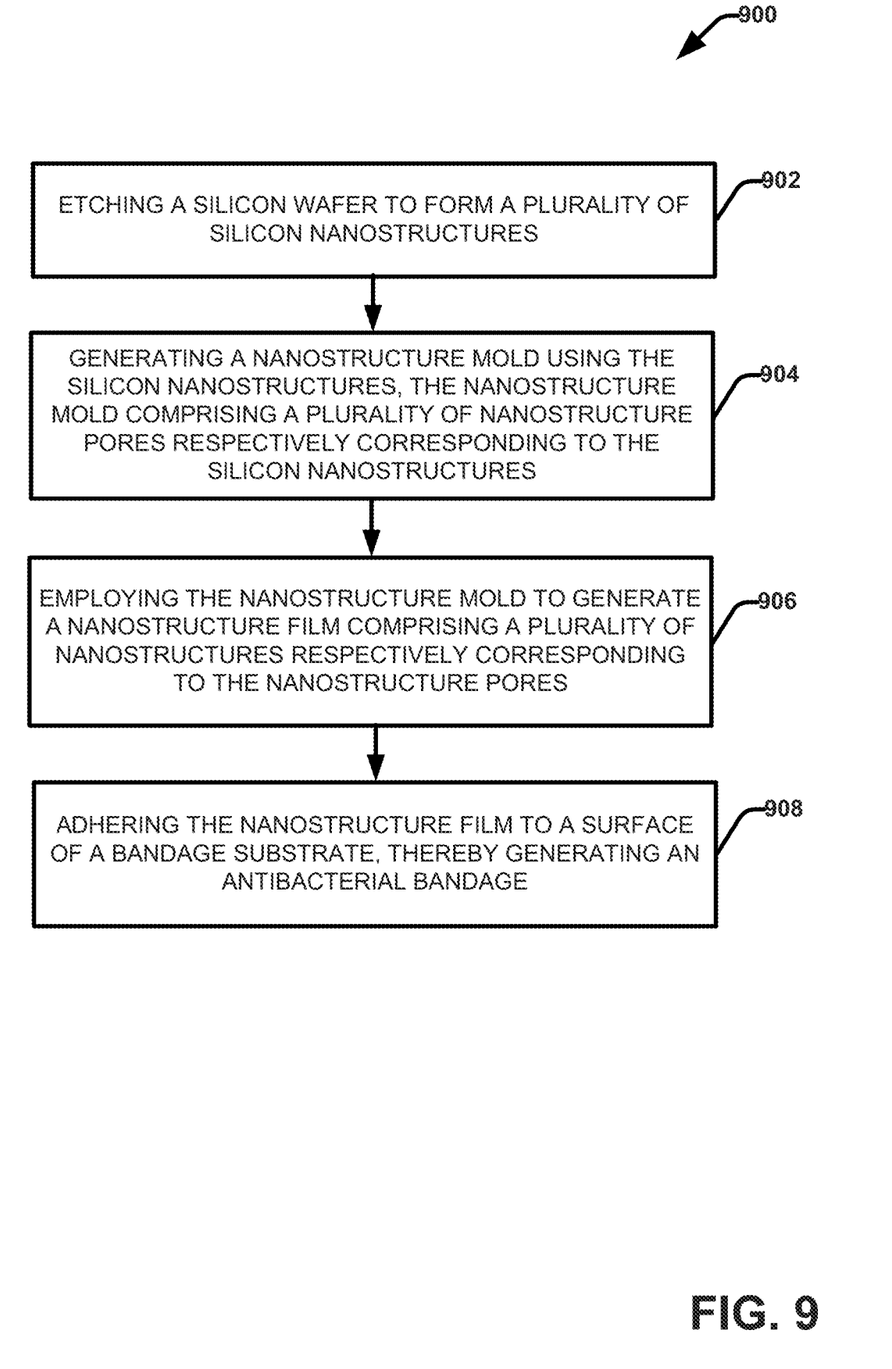
FIG. 9 provides a flow diagram of an example method that facilitates generating an antimicrobial bandage apparatus comprising a nanostructure layer in accordance with various embodiments described herein.
Figure 10:
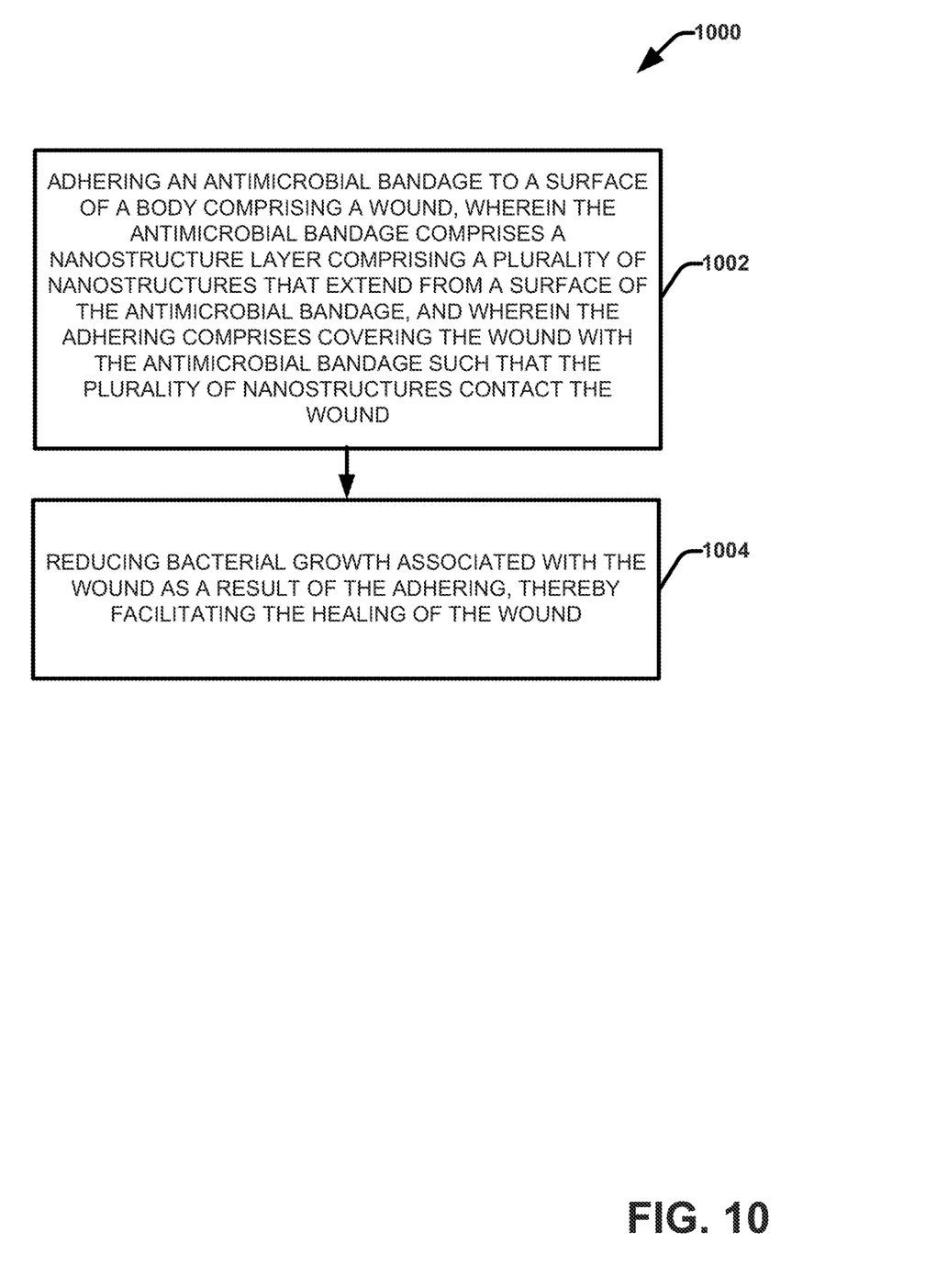
FIG. 10 provides a flow diagram of an example method that facilitates wound healing using an antimicrobial bandage apparatus in accordance with various embodiments described herein.

FIGS. 9-10 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts can occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts can be required to implement a methodology in accordance with the disclosed subject matter. Repetitive description of like elements employed in respective embodiments is omitted for sake of brevity.

FIG. 9 provides a flow diagram of an example method 900 for generating an antimicrobial bandage apparatus comprising a nanostructure layer in accordance with various embodiments described herein.

At 902, silicon wafer is etched to form a plurality of silicon nanostructures. At 904, a nanostructure mold is generated using the silicon nanostructures, the nanostructure mold comprising a plurality of nanostructure pores respectively corresponding to the silicon nanostructures. At 906, the nanostructure mold can be applied to generate a nanostructure film comprising a plurality of nanostructures respectively corresponding to the nanostructure pores. At 908, the nanostructure film can be adhered to a surface of a bandage substrate, thereby generating an antibacterial bandage.

FIG. 10 provides a flow diagram of an example method 1000 that facilitates wound healing using an antimicrobial bandage apparatus in accordance with various embodiments described herein.

At 1002, an antimicrobial bandage is adhered to a surface of a body comprising a wound, wherein the antimicrobial bandage comprises a nanostructure layer comprising a plurality of nanostructures that extend from a surface of the antimicrobial bandage, and wherein the adhering comprises covering the wound with the antimicrobial bandage such that the plurality of nanostructures contact the wound. At 1004, bacterial growth associated with the wound is reduced as a result of the adhering, thereby facilitating the healing of the wound.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments described herein, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all embodiments falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A bandage, comprising:
a substrate comprising a first surface and a second surface opposing the first surface; an adhesive layer provided on the first surface that is configured to facilitate removably attaching the substrate to an epithelial layer associated with a wound; and
a nanostructure film provided on the first surface, the nanostructure film comprising a plurality of nanostructures wherein respective nanostructures of the plurality of nanostructures comprise a nanospike geometry and wherein the plurality of nanostructures are formed from a material that is configured to have rigidity to puncture and mechanically rupture bacterial cells proximate the wound and to have flexibility to bend over and around a curved surface of the body without breaking such that the plurality of nanostructures are configured to contact the wound without puncturing the wound when the substrate is attached to the epithelial layer.

2. The bandage of claim 1, wherein the substrate comprises a flexible material that is configured to bend or wrap around a part of a body comprising the wound.

3. The bandage of claim 1, wherein the nanostructure film comprises a polymer material.

4. The bandage of claim 1, wherein the plurality of nanostructures respectively has a pitch between about 100 nanometers and about 2.0 micrometers.

5. The bandage of claim 1, wherein the plurality of nanostructures respectively has a height between about 100 nanometers and about 10.0 micrometers.

6. The bandage of claim 1, wherein the substrate comprises a polymer material, a rubber material, a fabric, a paper based material, or a combination thereof.

7. A bandage apparatus, comprising:
a substrate comprising a first surface and a second surface opposing the first surface: an attachment mechanism provided on the first surface that is configured to facilitate removably attaching the substrate to a part of a body comprising a wound; and
a nanostructure film provided on the first surface comprising a plurality of nanostructures wherein respective nanostructures of the plurality of nanostructures comprise a nanospike geometry and wherein the plurality of nanostructures are formed from a material that is configured to have rigidity to puncture and mechanically rupture bacterial cells proximate the wound and to have flexibility to bend over and around a curved surface of the body without breaking such that the plurality of nanostructures are configured to contact the wound without puncturing the wound when the substrate is attached to the part of the body comprising the wound.

8. The bandage apparatus of claim 7, wherein respective nanostructures of the plurality of nanostructures comprise a proximal end on the first surface of the substrate and a distal end that extends away from the proximal end, and wherein the respective nanostructures have a diameter that tapers from the proximal end to the distal end.

9. The bandage apparatus of claim 8, wherein the distal end has a first diameter between about 1.0 nanometers and about 200 nanometers.

10. The bandage apparatus of claim 8, wherein the proximal end has a second diameter between about 1.0 nanometers to about 1.0 micrometers.

11. The bandage apparatus of claim 7, wherein respective nanostructures of the plurality of nanostructures have a pitch between about 100 nanometers and about 2.0 micrometers.

12. The bandage apparatus of claim 7, wherein respective nanostructures of the plurality of nanostructures have a height between about 100 nanometers and about 10.0 micrometers.

13. The bandage apparatus of claim 7, wherein the substrate and the nanostructure film comprise a flexible material.

14. The bandage apparatus of claim 7, wherein the nanostructure film comprises a polymer material.

15. A method of mitigating bacterial infections associated with wounds, comprising: providing a bandage apparatus including a substrate, an attachment mechanism, and a nanostructure film comprising a plurality of nanostructures wherein respective nanostructures of the plurality of nanostructures comprise a nanospike geometry and wherein the plurality of nanostructures are formed from a material that is configured to have rigidity to puncture and mechanically rupture bacterial cells proximate a wound and to have flexibility to bend over and around a curved surface of a body without breaking such that the plurality of nanostructures are configured to contact the wound without puncturing the wound when the substrate is attached to a part of the body comprising the wound, wherein the attachment mechanism and the nanostructure film are each provided on a first surface of the substrate that opposes a second surface of the substrate.

16. The method of claim 15, wherein the plurality of nanostructures respectively has a pitch between about 100 nanometers and about 2.0 micrometers, and a height between about 100 nanometers and about 10.0 micrometers.

* * * * *